(12) United States Patent
Helmlinger (10) Patent No.: US 10,065,006 B2
(45) Date of Patent: Sep. 4, 2018

(54) DISPENSER HAVING A SYSTEM FOR DETECTING DISCHARGE PROCESSES

(71) Applicant: APTAR RADOLFZELL GMBH, Radolfzell (DE)

(72) Inventor: Michael Helmlinger, Radolfzell-Boehringen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 15/119,239

(22) PCT Filed: Jan. 30, 2015

(86) PCT No.: PCT/EP2015/051988
§ 371 (c)(1),
(2) Date: Aug. 16, 2016

(87) PCT Pub. No.: WO2015/139874
PCT Pub. Date: Sep. 24, 2015

(65) Prior Publication Data
US 2017/0007783 A1    Jan. 12, 2017

(30) Foreign Application Priority Data

Mar. 17, 2014 (DE) .......................... 10 2014 204 940

(51) Int. Cl.
*A61M 15/00* (2006.01)
*B05B 11/00* (2006.01)
(Continued)

(52) U.S. Cl.
CPC .......... *A61M 15/008* (2014.02); *A61M 11/02* (2013.01); *A61M 15/009* (2013.01);
(Continued)

(58) Field of Classification Search
CPC ............ A61M 15/008; A61M 2205/52; A61M 2205/70; A61M 15/009;
(Continued)

(56) References Cited

U.S. PATENT DOCUMENTS 6,651,651 B1   11/2003  Bonney et al.
7,661,557 B2   2/2010   Volker et al.
(Continued)

FOREIGN PATENT DOCUMENTS

DE          699 28 267 T2    6/2006
DE    10 2006 036 962 A1    2/2008
(Continued)

OTHER PUBLICATIONS

International Search Report issued in Application No. PCT/EP2015/051988 with English translation, dated Apr. 30, 2015 (7 pages).
(Continued)

*Primary Examiner* — Nicholas J Weiss
(74) *Attorney, Agent, or Firm* — Flynn, Thiel, Boutell & Tanis, P.C.

(57) ABSTRACT

Dispenser for the discharge of pharmaceutical media having a liquid storage, a base body, an actuating handle that is manually displaced with respect to the base body for causing a discharge process of media from the liquid storage into an environment, and an electronic detection system for detecting discharge processes. A sensor is provided, which, subject to the displacement of a reference component mechanically coupled to the actuating handle such that during a discharge process the reference component is displaced with respect to the base body, generates an output signal. The sensor is configured for generating output signals of two distinguishable types as a function of the extent of the displacement,
(Continued)

and is provided with an electronic calibration memory in which calibration data regarding discharge behavior of the dispenser are stored.

18 Claims, 4 Drawing Sheets

(51) Int. Cl.
  *G01D 5/14* (2006.01)
  *A61M 11/02* (2006.01)
  *A61M 16/20* (2006.01)

(52) U.S. Cl.
  CPC ........ *B05B 11/0067* (2013.01); *B05B 11/307* (2013.01); *B05B 11/308* (2013.01); *G01D 5/14* (2013.01); *A61M 16/201* (2014.02); *A61M 2205/3317* (2013.01); *A61M 2205/3331* (2013.01); *A61M 2205/3584* (2013.01); *A61M 2205/52* (2013.01); *A61M 2205/70* (2013.01)

(58) Field of Classification Search
  CPC .. A61M 2205/3317; A61M 2205/3331; A61M 2205/3584; A61M 11/02; A61M 16/201; B05B 11/308; B05B 11/307; B05B 11/0067; G01D 5/14
  See application file for complete search history.

(56) References Cited

U.S. PATENT DOCUMENTS

| | | |
|---|---|---|
| 7,849,851 B2 | 12/2010 | Zierenberg et al. |
| 8,997,735 B2 | 4/2015 | Zierenberg et al. |
| 9,204,994 B2 | 12/2015 | Greiner-Perth et al. |
| 2005/0247305 A1 | 11/2005 | Zierenberg et al. |
| 2008/0029539 A1 | 2/2008 | Volker et al. |
| 2010/0192948 A1 | 8/2010 | Sutherland et al. |
| 2011/0048415 A1 | 3/2011 | Zierenberg et al. |
| 2013/0190703 A1 | 7/2013 | Greiner-Perth et al. |

FOREIGN PATENT DOCUMENTS

| | | |
|---|---|---|
| DE | 10 2010 048 085 A1 | 4/2012 |
| GB | 2 451 833 A | 2/2009 |
| WO | WO 2004/091806 A1 | 10/2004 |
| WO | WO 2005/080001 A1 | 9/2005 |

OTHER PUBLICATIONS

Written Opinion of International Searching Authority issued in Application No. PCT/EP2015/051988 dated Apr. 30, 2015 (8 pages).

Examination Report of German Patent Office issued in Application No. 10 2014 204 940.7 dated Jan. 28, 2015 (2 pages).

DISPENSER HAVING A SYSTEM FOR DETECTING DISCHARGE PROCESSES

FIELD OF USE AND PRIOR ART

The invention relates to a dispenser for discharging pharmaceutical media, with a liquid reservoir, a base body, an actuating handle which is displaceable with respect to the base body in order to cause a process by which medium is discharged from the liquid reservoir into an environment, and an electronic detection system for detecting discharge processes.

Dispensers of the type in question are generally known from the prior art. For example, DE 10 2006 036 962 A1 proposes a dispenser with a counting module which provides the user with information concerning discharge processes that have already been performed. This counting module counts the occurrence of relative displacements of component parts of the dispenser that are manually displaced relative to each other during a discharge process.

A problem that has arisen in the past with dispensers of the type in question is that it is difficult to exactly coordinate the detection system with the discharge process. This means that there is the danger of a supposed discharge process being detected that has not in fact actually taken place, since the actuating handle has not been displaced sufficiently far. The problem can also be seen in the sense of a discharge process having taken place but not having been detected, since a sufficient displacement of the actuating handle for this has not taken place.

It has been shown that this problem therefore arises especially since component tolerances on the dispenser lead to slightly deviating actuation distances of the actuating handle until the commencement of a discharge process. It can thus happen that two dispensers intended to be of the same design differ from each other in terms of their behavior in reaction to an actuation of the actuating handle in such a way that, with the identical displacement path, a discharge process takes place in the case of one of the dispensers, whereas no discharge process takes place in the case of the other dispenser.

OBJECT AND SOLUTION

The object of the invention is to make available a dispenser which overcomes the above problem caused in particular by component tolerances.

According to the invention, this is achieved by the fact that the detection system has a sensor which generates an output signal depending on the displacement of a reference component that is mechanically coupled to the actuating handle, wherein the sensor is configured to generate output signals of at least two distinguishable types as a function of the extent of the displacement. Moreover, the detection system of a dispenser according to the invention has an electronic calibration memory, in which calibration data concerning the discharge behavior of the dispenser are stored.

Thus, in a dispenser according to the invention, an actuating handle is provided by means of which a discharge process can be brought about manually. This operative coupling can be provided, for example, by a piston pump being actuated by means of the actuating handle or by an outlet valve being opened. The actuating handle is coupled to those components of the dispenser effecting the discharge process, in such a way that, assuming completely identical dispensers, the discharge process takes place in a precisely defined relative position of the actuating handle with respect to the base body, which relative position is identical for all dispensers of the same design.

The measures according to the invention help achieve a processing of the discharge processes with a low error rate, even though the relative position of the actuating handle with respect to the base body, starting from which the discharge process begins, differs between different dispensers of a same type. The sensor provided according to the invention, and directly detecting the relative movement between the actuating handle and the base body or else the relative movement between a reference component positively coupled to the actuating handle in another way and the base body, is able to output at least two different types of signals depending on the extent of the displacement. A signal of the first type is output in the case of a first displacement extent. A signal of the second type is output in the case of a second displacement extent. Proceeding from an unactuated state of the dispenser, a manually induced displacement of the actuating handle thus initially leads to a sensor signal of a first type and then, as displacement continues, to a sensor signal of a second type. The signals preferably differ in terms of the electrical voltage.

The number of the distinguishable types of signals is preferably much higher than two, for example at least eight types of signals. In particular, the sensor is preferably configured to output an analog signal that changes constantly along the displacement path of the actuating handle or of the reference component, such that, as it were, there is an infinite number of signal types that the sensor is able to generate. Such an analog configuration is obtained, for example, if a potentiometer is provided which acts as voltage divider and which makes available a voltage value that is variable as a function of the displacement of the reference component with respect to the base body.

In the case of different dispensers of the same type which, on account of component tolerances and variations in the material properties, allow the discharge process to begin in different relative positions of the actuating handle, the different types of signals that can be output by the sensor make it possible to evaluate in each case different signal types to establish that the discharge process has begun.

For this purpose, according to the invention, the electronic calibration memory is moreover provided in which calibration data concerning the discharge behavior of the specific dispenser are stored. These calibration data are data that relate to the individual dispenser and that do not have to be identical between two dispensers of the same type. These calibration data represent the individual particularities of an individual dispenser in respect of its behavior in reaction to a displacement of the actuating handle. The detection system can have an evaluation device for processing the output signals, which evaluation device evaluates the discharge process taking account of the type of the output signal. This means that the evaluation device is designed such that it is able to use not just the presence of a signal obtained by a displacement of the actuating handle of any desired extent for the evaluation, but also the type of the signal that can be obtained in a different way by said configuration of the sensor.

Provision is made in particular that the evaluation device comprises a counting device or is configured as such, wherein this counting device evaluates a performed discharge process by taking account of the type of the output signal of the sensor and taking account of data stored in the calibration memory.

This counting device thus takes account not just of the output signal of the sensor or the type of this output signal, but also values that are stored individually in the calibration memory for the dispenser. These values provide information on what extent of displacement of the actuating handle relative to the base body is needed in the specific dispenser in order to initiate a discharge process, or information on what type of output signal is expected from the sensor when the discharge process actually begins.

Thus, in a greatly simplified representation, it is possible, for example, to store in the memory the fact that the potentiometer forming the sensor has a partial voltage between one end of the resistance layer and a sliding contact of the potentiometer, lying at 2.5 V when the discharge process begins. When the displacement of the actuating handle with respect to the base body takes place, the partial voltage is interrogated at short intervals by the detection system, but the result is not processed if the measured partial voltage is below said value of 2.5 V. It is only at 2.5 V, and thus precisely at the moment the discharge process begins, that the value stored in the calibration memory is reached or exceeded and, in this way, a counting process is performed which, for example, could lie in the advancement of a counting register by the value of 1.

The sensor is in particular preferably arranged directly between the component forming the actuating handle and the base, such that its output value changes depending on the relative movement of these two components. However, the invention also covers designs in which the sensor is arranged between the base and an intermediate component, in which case the intermediate component is mechanically positively coupled to the actuating handle.

As regards the type of the dispenser according to the invention, various configurations are conceivable. Thus, the actuating handle of a dispenser according to the invention can be mechanically coupled to a pump device which has a volumetrically variable pump chamber, of which the volume can be decreased by actuation of the actuating handle. In such a dispenser, a batch of the medium that is to be discharged is thus subjected to pressure for the purpose of discharge and then escapes from the dispenser. Normally and preferably, such a dispenser has an outlet valve that opens depending on pressure and is arranged on the other side of the pump chamber, which is opened by the action of pressure by the liquid in the pump chamber. In a dispenser with a pump device and in particular one with an outlet valve that opens depending on pressure, there are a great many influencing factors that can lead to a situation where dispensers of the same type nevertheless begin the discharge process in different positions of the actuating handle. The configuration according to the invention with a calibration memory with dispenser-specific behavior stored therein is therefore advantageous specifically in this type of dispenser.

However, a dispenser according to the invention can also be configured in such a way that the actuating handle is mechanically coupled to an outlet valve without interposition of a pressurized fluid, which outlet valve can be opened by displacement of the actuating handle. In such a dispenser, the actuating handle thus acts on the outlet valve not indirectly via the pressure of the liquid in the pump chamber, but directly by mechanical coupling. However, in this type of dispenser too, there are many influencing factors that can lead to a situation where different relative positions of the actuating handle with respect to the base body can start the discharge process in dispensers of the same type.

The dispensers of the last-mentioned type can in particular also be dispensers in whose liquid reservoir the medium to be discharged is stored under pressure. The outlet valve can in particular be coupled to a dosing chamber which separates an always substantially constant quantity of the medium from the medium remaining in the liquid reservoir and dispenses it during the actuation of the outlet valve.

Moreover, the invention also relates to a method for producing a dispenser of the type designated at the outset. In this method, an actuation of the dispenser takes place in an automated manner by means of a calibration device not belonging to the dispenser, and the behavior of the dispenser is detected. Thereafter, data representing the detected behavior of the dispenser are stored in the calibration memory of the dispenser.

For this purpose, a dispenser according to the invention preferably has an electronic interface which is accessible from the outside and by means of which a calibration process can be triggered. When a signal is sent to the CPU of the dispenser via this interface, it writes the sensor value currently detected on the sensor into the calibration memory of the dispenser.

In said method, provision is made that a calibration procedure is carried out even during the process of producing the dispenser, by means of which the behavior of a specific dispenser is detected. This can in particular involve a detection of the start of a discharge process as a function of the relative position of the actuating handle with respect to the base body. However, an alternative or additional detection of the position of the actuating handle at the conclusion of the discharge process is also conceivable. This value determined individually for the dispenser is then written into the calibration memory, such that it is then available for consideration in the detection of discharge processes with this dispenser.

The invention moreover also relates to a method for operating a dispenser according to the invention, said method being characterized by the following method steps in reaction to an actuation of the dispenser. The extent of the displacement of the reference component with respect to the base body is detected by said sensor. Thereafter, the actuation performed is categorized by comparing this extent with data from the calibration memory. A processing step in the form of a counting process is then performed or not performed, depending on the categorization. The method is in particular carried out repeatedly at short time intervals during one and the same actuation, for example at an interval of 50 milliseconds.

BRIEF DESCRIPTION OF THE DRAWINGS

Further aspects and advantages of the invention will become clear from the claims and from the following description of a preferred illustrative embodiment of the invention. The preferred illustrative embodiment is explained with reference to the figures, in which:

DETAILED DESCRIPTION OF THE ILLUSTRATIVE EMBODIMENTS

Figure 1:
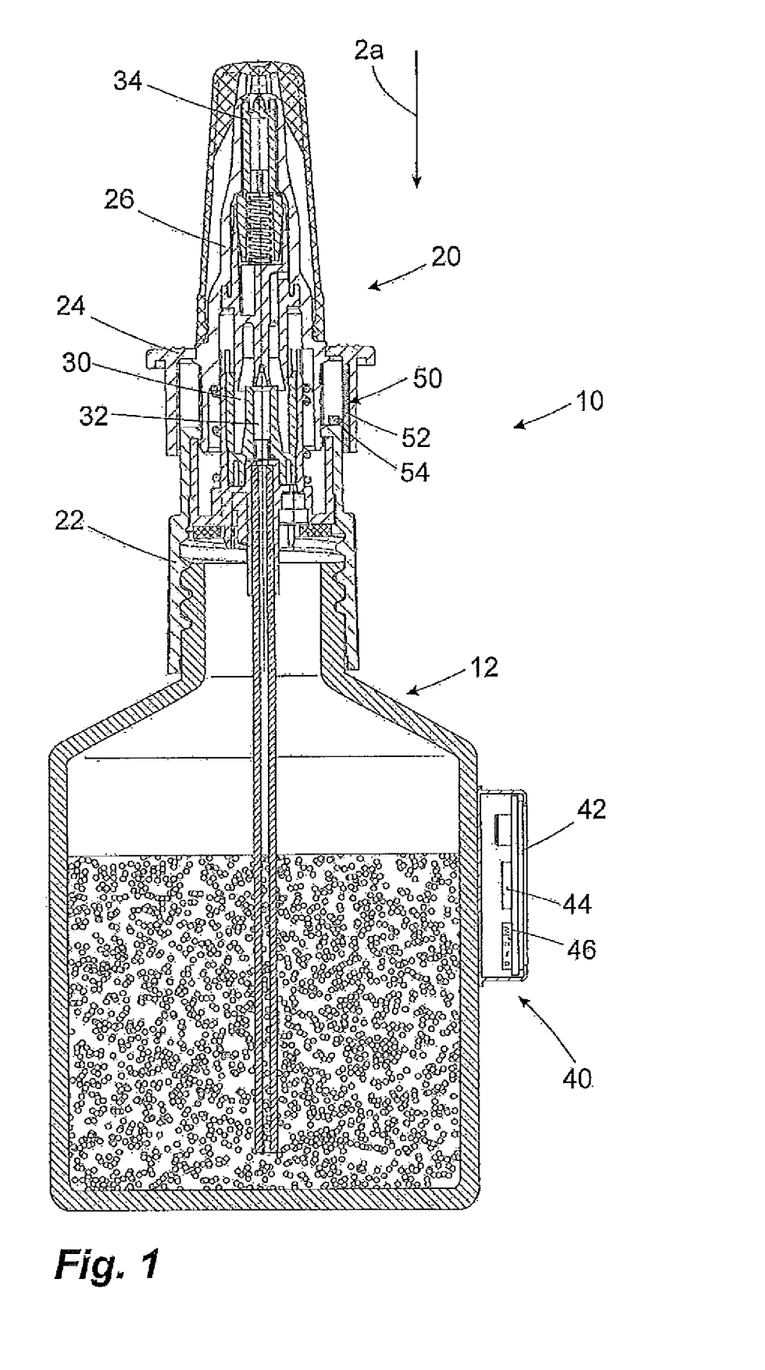
FIG. 1 shows a first embodiment of a dispenser according to the invention.
Figure 2:
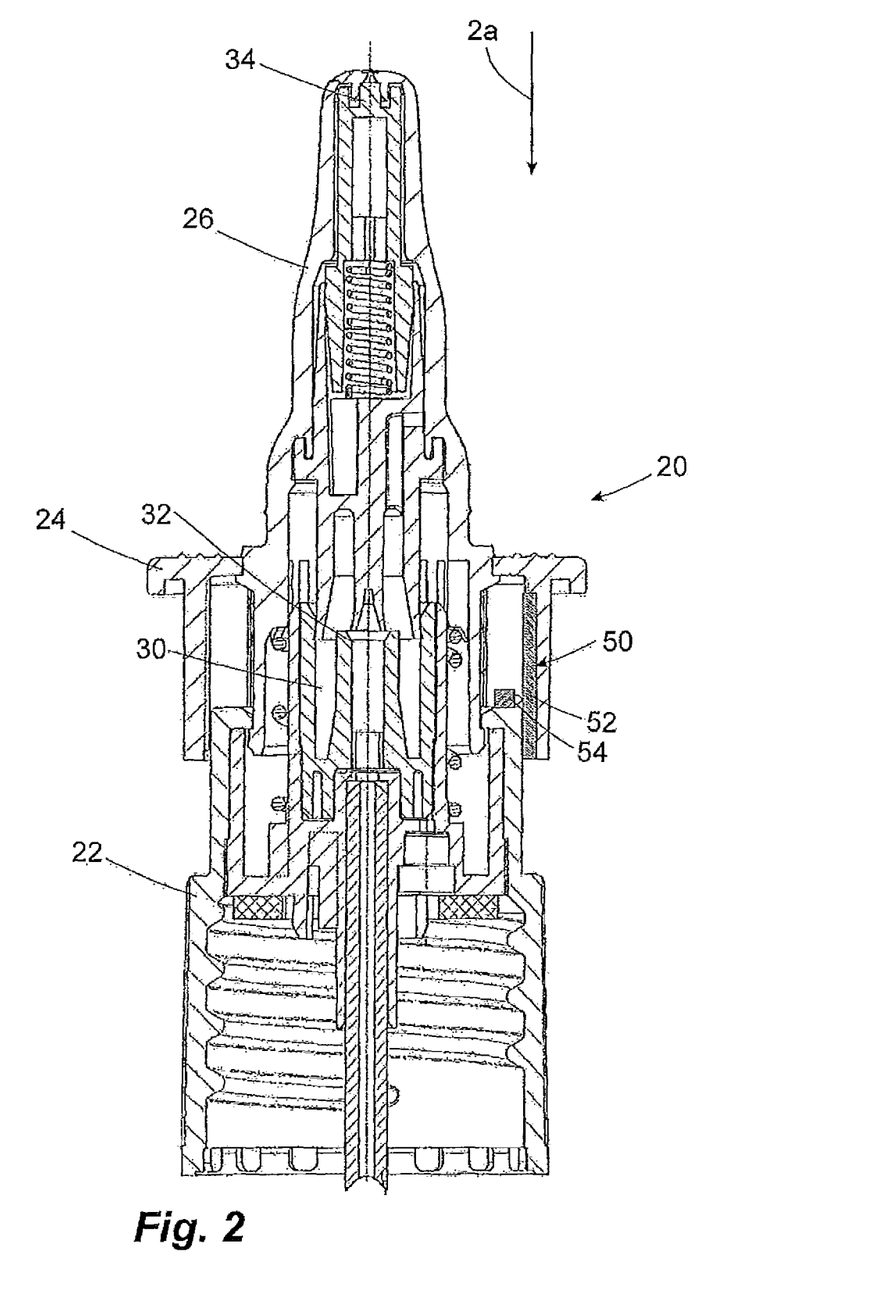
FIG. 2 shows an enlarged view of the discharge head of the dispenser from FIG. 1.

FIGS. 1 and 2 show a first embodiment of a dispenser according to the invention and also the discharge head thereof in an enlarged view.

In terms of its liquid-conveying parts, the dispenser 10 does not differ from conventional dispensers. Its specific design is to be understood as an example.

The dispenser 10 has a liquid reservoir 12 and a discharge head 20. This discharge head 20 has a base body 22 screwed onto the liquid reservoir 12, and also an actuating handle 24 which is displaceable relative to the base body 22 and which also comprises a nosepiece 26 with discharge opening.

The liquid reservoir 12 is intended to store the pharmaceutical liquid that is to be discharged, before the discharge. For the purpose of the discharge, the discharge head 20 has a pump chamber 30 which, on the inlet side, is connected by a slide valve 32 to the liquid reservoir 12 and which, on the outlet side, has a valve 34 that opens depending on pressure.

To actuate this dispenser, the actuating handle 24 is pressed down in the direction of the arrow 2a, as a result of which a closure of the inlet valve 32 is brought about. As soon as the inlet valve 32 is closed, a continued displacement of the actuating handle 24 in the downward direction leads to a pressure increase of the liquid located in the pump chamber 30, which in turn causes the outlet valve 34 to open and subsequently brings about a discharge process.

The dispenser of FIG. 1 differs from purely mechanical dispensers in terms of the presence of an electronic counting device 40 which, in reaction to a performed discharge process, is intended to advance a counting register and displays the result on a display device 42.

The detection of the discharge process with the counting device 40 is intended to take place only when the discharge process has actually begun, not when the displacement of the actuating handle 24 relative to the base body 22 has been insufficient for a discharge process.

To enable the counting device 40 to detect whether the displacement of the actuating handle has been sufficient to generate a discharge process, a sensor 50 is provided which detects the relative movement of the actuating handle 24 with respect to the base body 22. The sensor 50 is configured as a potentiometer and has a resistance layer 52 and a sliding contact 54. The potentiometer acts as a voltage divider. A voltage of 5 V, for example, is present between the two opposite ends of the resistance layer 52. The partial voltage thereof between the lower end of the resistance layer 52 and the sliding contact 54 increases with increasing downward displacement of the actuating handle 24 in the direction of the arrow 2a.

The potentiometer is connected, in a manner not shown in detail, to a CPU 44 of the counting device 40, which is able to detect the partial voltage between the sliding contact 54 and the lower end of the resistance layer 52, said partial voltage resulting from the relative position of the sliding contact 54 with respect to the resistance layer 52. Since the sliding contact 54 is mounted on the base body 22 and the resistance layer 52 is on the actuating handle 24, said partial voltage is changed continuously during the actuation movement in the direction of the arrow 2a. The CPU 44 evaluates the partial voltage and compares the value with a voltage value stored in the memory 46, purely by way of example a value of 2.5 V in the present case. This partial voltage increases with increasing displacement of the actuating handle 24 relative to the base body 22. If the limit value of 2.5 V stored in the memory 46 is exceeded, said counting step is performed by the CPU 44 and the result is shown on the display device 42.

The respective limit value stored in the memory 46 depends on the individual dispenser in each case. The memory is therefore preferably a write-once memory or a rewriteable memory. The value has been determined, in a manner described in more detail below, during the production process and has been stored in the memory.

The value provided in a manner specific to the dispenser reduces the danger of an actually performed discharge process mistakenly not being counted or of a displacement of the actuating handle 24 with respect to the base body 22 being counted despite the non-occurrence of the discharge process.

Figure 3:
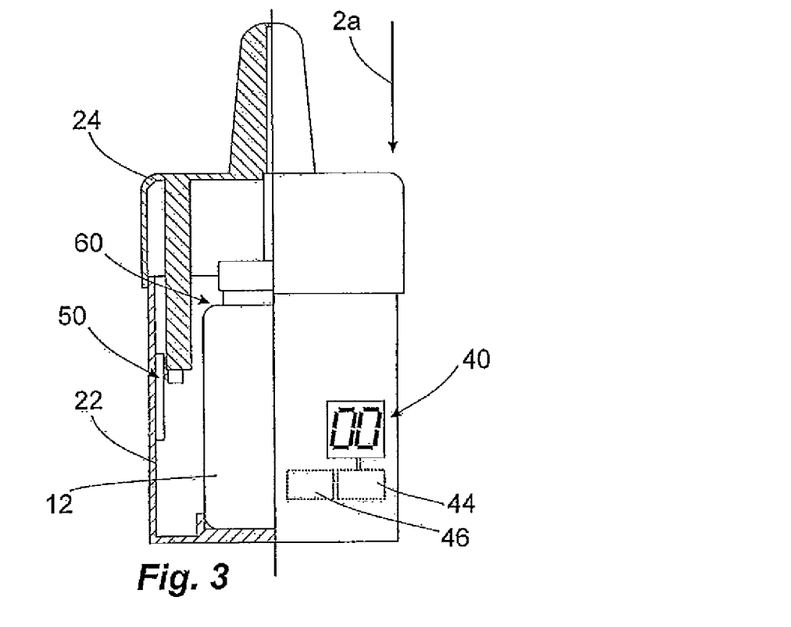
FIG. 3 shows a second embodiment of a dispenser according to the invention.

In terms of the presence of a counting device 40 and of a sensor 50 configured as a potentiometer, the discharge device in FIG. 3 is substantially identical to the embodiment in FIGS. 1 and 2. However, the design of this dispenser is fundamentally different since it has no pump chamber. The housing, which is formed by a base body 22 and by an actuating handle 24, accommodates a pumping dispenser 60, which for its part has a liquid reservoir 12. The liquid to be discharged is stored under pressure in this liquid reservoir 12. A discharge process can be effected by means of an outlet nozzle being pressed down together with the actuating handle 24. This causes an outlet valve to open, such that a quantity of liquid metered beforehand in an internal dosing chamber is dispensed.

In this embodiment too, a CPU 44, taking account of a voltage value stored in a memory 46 in a dispenser-individual manner, evaluates whether the actuating handle 24 has been displaced sufficiently far that a discharge process can be expected to have taken place.

Figure 4:
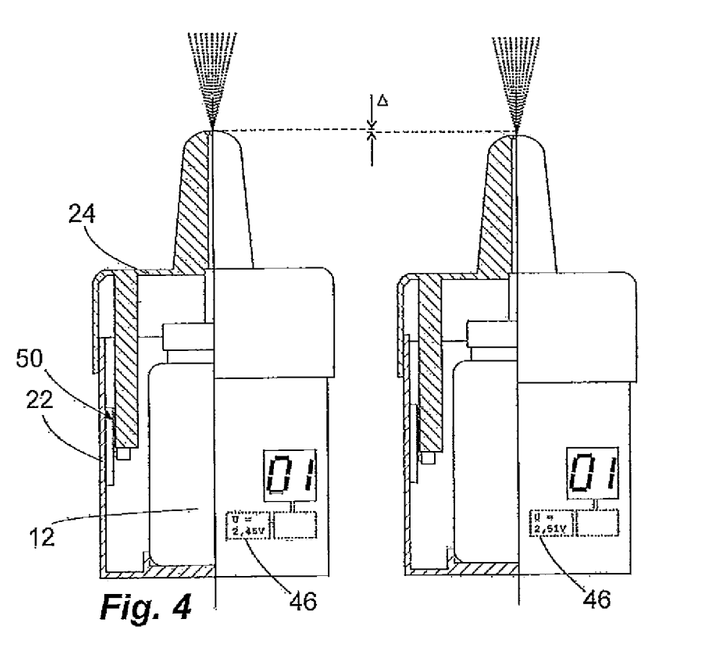
FIG. 4 shows two dispensers according to the invention that are of the same type but differ in behavior.

FIG. 4 illustrates that dispensers that are of the same type can differ in terms of the relative position of the actuating handle 24 with respect to the base body 22. The partial views on the left and right of FIG. 4 show such dispensers that are of the same type, in each case in a relative position of the actuating handle 24 with respect to the base body 22 in which the outlet valve of the pumping dispenser 60 opens. The indicated difference in travel Δ in the respectively required displacement paths of the actuating handle 24 influences the partial voltage on the sensor 50 between one end of the resistance layer 52 and the sliding contact 54 at the moment when the discharge process begins. Accordingly, different voltage values are also entered in the memory 46, and the CPU 44 compares these values with the value of the sensor 50 in order to detect whether a discharge process has taken place.

Figure 5:
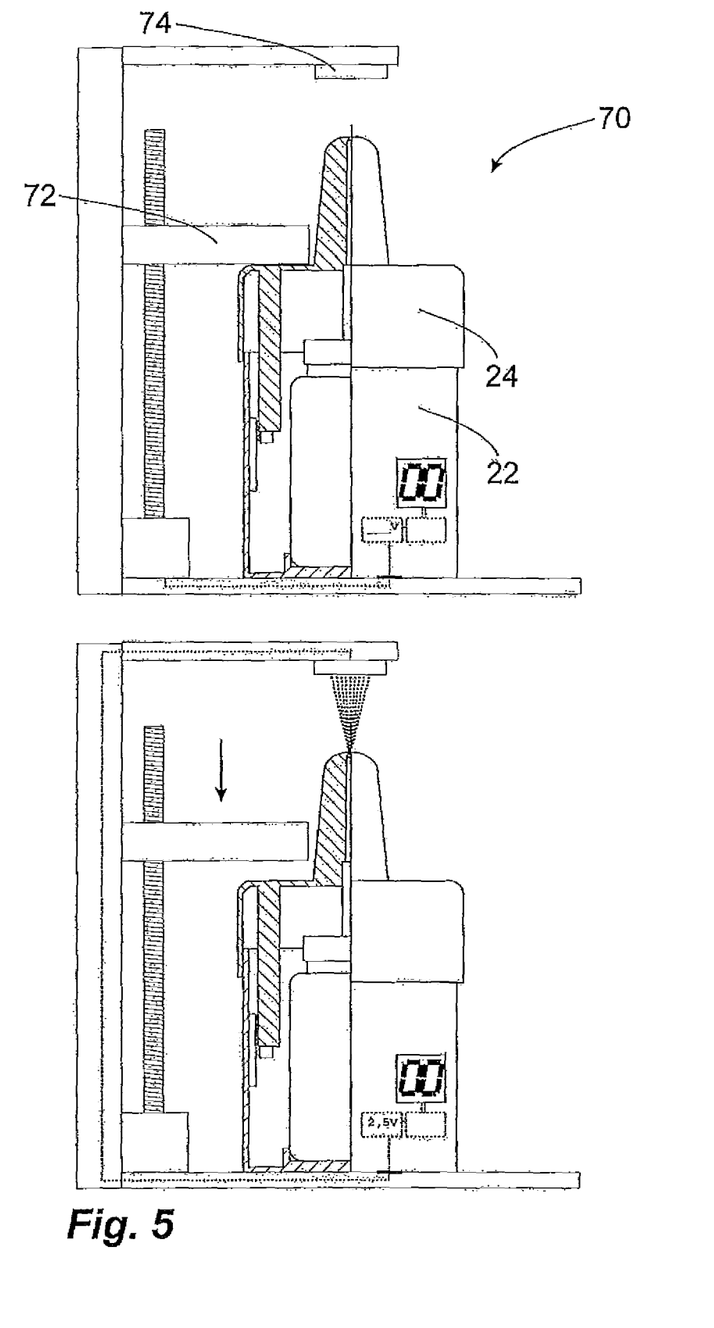
FIG. 5 shows the method for calibration of a dispenser according to the invention.

FIG. 5 shows schematically the method for calibrating the dispenser from FIGS. 3 and 4. This dispenser is inserted into a calibration device 70 which is designed to press the actuating handle 24 downward relative to the base body 22 by means of a movable pressure element 72. Above the discharge opening of the dispenser, a sensor 74 is provided which is able to detect the commencement of the discharge process. It can be designed, for example, as a humidity sensor or pressure sensor. While the discharge device 10 is inserted into the calibration device 70, a data connection between the CPU 44 and said sensor 74 is established. For this purpose, electrical contacts can be provided on the underside of the dispenser.

After insertion of the dispenser, the actuating pressure element 72 is displaced downward. As soon as the sensor 74 in the state in FIG. 5 registers the resulting discharge process and communicates this to the CPU 44, the latter writes the voltage value detected at that time by the sensor 50 into the memory 46. The dispenser is then calibrated.

The invention claimed is:

1. A dispenser for discharging pharmaceutical media, the dispenser comprising:
   a liquid reservoir;
   a base body;
   an actuating handle which is manually displaceable with respect to the base body in order to cause a process involving discharge of medium from the liquid reservoir into an environment; and
   an electronic detection system for detecting discharge processes;
   wherein the detection system has:
   a sensor which generates output signals depending on the displacement of a reference component that is mechanically coupled to the actuating handle such that the reference component is displaced with respect to the base body during a discharge process, wherein the output signals are of at least two distinguishable types as a function of an extent of the displacement of the reference component, and
   an electronic calibration memory in which calibration data concerning discharge behavior of the dispenser are stored.

2. The dispenser as claimed in claim 1, wherein:
   the detection system has an evaluation device for processing the output signals, the evaluation device evaluating the discharge process by taking account of the types of the output signals.

3. The dispenser as claimed in claim 2, wherein:
   the evaluation device is configured as a counting device which evaluates the discharge process by taking account of the types of the output signals and taking account of the calibration data stored in the calibration memory.

4. The dispenser as claimed in claim 1, wherein:
   the output signals are analog output signals.

5. The dispenser as claimed in claim 1, wherein:
   the actuating handle is mechanically coupled to a pump device which has a volumetrically variable pump chamber, of which a volume of the pump chamber can be decreased by the actuating handle.

6. The dispenser as claimed in claim 1, wherein:
   the actuating handle is mechanically coupled to an outlet valve which can be opened by displacement of the actuating handle.

7. A method for producing the dispenser with the calibration memory as claimed in claim 1, comprising:
   a. actuating the dispenser in an automated manner by a calibration device not assigned to the dispenser, wherein the behavior of the dispenser is detected; and
   b. storing data representing the detected behavior of the dispenser in the calibration memory of the dispenser.

8. The method as claimed in claim 7, wherein:
   the detection of the behavior of the dispenser involves detecting a relative position of the reference component to the base body in which, during the actuation:
   the discharge of the medium begins and/or
   the discharge of the medium is concluded.

9. A method for operating the dispenser as claimed in claim 1, wherein, upon actuation of the dispenser,
   a. the extent of the displacement of the reference component with respect to the base body is detected,
   b. the actuation is categorized by comparing the extent of the displacement with data from the calibration memory, and
   c. a counting process is performed or not performed, depending on the categorization.

10. The dispenser as claimed in claim 4, wherein:
    the sensor is configured as a potentiometer.

11. The dispenser as claimed in claim 1, wherein:
    the calibration data represents particularities of the dispenser with respect of the discharge behavior thereof in reaction to a displacement of the actuating handle.

12. A discharging system for discharging pharmaceutical media, the discharging system comprising:
    a dispenser including a liquid reservoir, a base body, an actuating handle and an electronic detection system within the dispenser;
    the actuating handle being manually displaceable with respect to the base body in order to cause a process involving discharge of medium from the liquid reservoir into an environment;
    the electronic detection system detecting discharge processes and including a sensor and an electronic calibration memory;
    the sensor generates output signals depending on the displacement of a reference component that is mechanically coupled to the actuating handle such that the reference component is displaced with respect to the base body during the discharge process, wherein the output signals are of at least two distinguishable types as a function of an extent of the displacement of the reference component; and
    the electronic calibration memory stores calibration data concerning discharge behavior of the dispenser representing particularities of the dispenser with respect of the discharge behavior thereof in reaction to a displacement of the actuating handle.

13. The discharging system as claimed in claim 12, wherein:
    the electronic detection system has an evaluation device for processing the output signals, the evaluation device evaluating the discharge process by taking account of the types of the output signals.

14. The discharging system as claimed in claim 13, wherein:
    the evaluation device is configured as a counting device which evaluates the discharge process by taking account of the types of the output signals and taking account of the calibration data stored in the electronic calibration memory.

15. A method for producing the discharging system as claimed in claim 12, comprising:
    a. actuating the dispenser in an automated manner by a calibration device not assigned to the dispenser, wherein the discharge behavior of the dispenser is detected; and
    b. storing data representing the detected behavior of the dispenser in the electronic calibration memory of the dispenser.

16. The method as claimed in claim 15, wherein:
    the detection of the discharge behavior of the dispenser involves detecting a relative position of the reference component to the base body in which, during the actuation:
    the discharge of the medium begins and/or
    the discharge of the medium is concluded.

17. A method for operating the discharging system as claimed in claim 12, wherein, upon actuation of the dispenser,
    a. the extent of the displacement of the reference component with respect to the base body is detected, b. the actuation is categorized by comparing the extent of the displacement with data from the electronic calibration memory,
c. a counting process is performed or not performed, depending on the categorization.

18. The discharging system as claimed in claim 12, wherein:
the electronic calibration memory is fixed to the liquid reservoir.

* * * * *